(12) United States Patent
Tomes et al.

(10) Patent No.: US 7,193,130 B2
(45) Date of Patent: Mar. 20, 2007

(54) EXPRESSING ACID INVERTASE OR ADP-GLUCOSE PYROPHOSPHORYLASE IN FLORAL TISSUE FOR ENHANCED FLORAL SINK STRENGTH AND INCREASED STABILITY OF SEED IN PLANTS

(75) Inventors: Dwight T. Tomes, Van Meter, IA (US); Christopher Zinselmeier, Des Moines, IA (US); Jeffrey E. Habben, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 233 days.

(21) Appl. No.: 10/462,465

(22) Filed: Jun. 16, 2003

(65) Prior Publication Data
US 2003/0217387 A1    Nov. 20, 2003

Related U.S. Application Data

(63) Continuation of application No. 09/599,353, filed on Jun. 20, 2000, now abandoned.

(60) Provisional application No. 60/140,314, filed on Jun. 21, 1999.

(51) Int. Cl.
*C12N 15/82* (2006.01)
(52) U.S. Cl. .................................. 800/278; 435/320.1
(58) Field of Classification Search ............. 435/320.1; 800/298, 284
See application file for complete search history.

(56) References Cited

U.S. PATENT DOCUMENTS

| 5,436,394 | A | * | 7/1995 | Willmitzer et al. | ......... 800/284 |
| 5,608,149 | A | * | 3/1997 | Barry et al. | ................. 800/284 |
| 5,658,773 | A | | 8/1997 | Bennett et al. | .......... 435/172.3 |
| 5,716,837 | A | * | 2/1998 | Barry et al. | ................. 800/284 |
| 5,914,449 | A | * | 6/1999 | Murase et al. | ............. 800/281 |
| 6,013,862 | A | * | 1/2000 | Simmonds et al. | ......... 800/287 |
| 6,169,232 | B1 | * | 1/2001 | Hey et al. | ................. 800/320.1 |
| 6,232,529 | B1 | * | 5/2001 | Singletary et al. | .......... 800/281 |

FOREIGN PATENT DOCUMENTS

| WO | WO 92/14831 | 9/1992 |
| WO | WO 93/09237 | 5/1993 |
| WO | WO 96/14421 | 5/1996 |
| WO | WO 96/21738 | 7/1996 |
| WO | WO 97/15678 | 5/1997 |
| WO | WO 97/20936 | 6/1997 |
| WO | WO 98/08961 | 3/1998 |
| WO | WO 98/10082 | 3/1998 |
| WO | WO 98/44780 | 10/1998 |
| WO | WO 99/29881 | 6/1999 |
| WO | WO 00/11177 | 3/2000 |

OTHER PUBLICATIONS

Weber, Hans, et al., "Expression of a Yeast-Derived Invertase in Developing Cotyledons of *Vicia narbonenesis* Alters the Carbohydrate State and Affects Storage Functions", *The Plant Journal*, (1998), pp. 163-172.

Xu, Jian, et al., "The *Ivr* 1 Gene for Invertase in Maize[1]", *Plant Physiology*, (1995), pp. 1293-1294.

Herbers, Karin, et al., "Molecular Determinants of Sink Strength", *Physiology and Metabolism*, (1998), pp. 207-216.

Zinselmeier, Chris, et al., "Low Water Potential Disrupts Carbohydrate Metabolism in Maize (*Zea mays* L.) Ovaries[1]", *Plant Physiology*, (1995), pp. 385-391.

Cheng, W.H., et al., "Genetic Evidence That Invertase-Mediated Release of Hexoses is Critical for Appropriate Carbon Partitioning and Normal Seed Development in Maize", *Program in Plant Molecular and Cellular Biology, University of Florida*, (1999), pp. 485-495.

Kosegarten, Harald, et al., "Starch Deposition In Storage Organs and the Importance of Nutrients and External Factors", *Dissertation. Institute of Plant Nutrition, Liebig University, Giessen. Germany*, (1998), pp. 273-287.

Xu, Jian, et al., "A Similar Dichotomy of Sugar Modulation and Development Expression of Affects Both Paths of Sucrose Metabolism: Evidence from a Maize Invertase Gene Family", *The Plant Cell*, vol. 8, (1996) pp. 1209-1220.

Miller, Michael E., et al., "The Maize Invertase-Deficient *miniature*-1 Seed Mutation is Associated with Aberrant Pedicel and Endosperm Development", *The Plant Cell*, 1992, vol. 4, pp. 297-305.

Otegui, Maria E., "Kernel Set and Flower Synchrony Within the Ear of Maize: II. Plant Population Effects", *Crop Science*, 1997, 37: pp. 448-455.

(Continued)

*Primary Examiner*—Anne Kubelik
(74) *Attorney, Agent, or Firm*—McKee, Voorhees & Sease, P.L.C.

(57) ABSTRACT

The invention discloses a transgenic method for enhancing sink strength in female reproductive organs. It involves the expression of nucleic acids encoding acid invertase or ADP-glucose pyrophosphorylase floral tissue. The invention also includes expression constructs used in the method.

2 Claims, 2 Drawing Sheets

OTHER PUBLICATIONS

Preiss, J., "Bacterial Glycogen Synthesis and Its Regulation", *Annual Review Microbiology*, 1984, 38: pp. 419-458.

Salibury, Frank B. et al., "Transport In the Phloem", *Plant Physiology 3rd Edition*, 1985, pp. 135-161.

Schmalstig, Judy Gougler et al., "Transport and Metabolism of a Sucrose Analog (1'-Fluorosucrose) Into *Zea mays* L . Endosperm Without Invertase Hydrolysis[1]", *Plant Physiology*, 1987, 85: pp. 902-905.

Schussler, J.R. et al., "Maize Kernel Set at Low Water Potential: II. Sensitivity to Reduced Assimilates at Pollination", *Crop Science*, 1991, 31: 1196-1203.

Schmidt, R.J. et al., "Identification and Molecular Characterization of ZAGI, The Maize Hormolog of the Arabidopsis fliral Homeotic Gene AGAMOUS", "Gene Expression in Cereal Crops", presented at the American Society of Plant Physiologists, 1993, pp. 729-737.

Shaw, Robert H., "Corn and Corn Improvement", *ASA-CSSA-SSSA*, 1988, pp. 609-639.

Sivak, M.N. et al., "Starch Synthesis In Seeds", *Seed Development and Germination*, 1994, pp. 139-168.

Stitt, Mark, "The Use of Transgenic Plants to Study the Regulation of Plant Carbohydrate Metabolism", Paper presented at symposium at the 34th Mtg of the Australian Society of Plant Physiologists, 1995, pp. 635-646.

Taiz, Lincol, 1991, *Plant Physiology*, Published by The Benjamin/Cummings Publishing Company, Inc. Redwood City, CA., pp. 125-175.

Weber, Hans et al., "Controlling Seed Development and Seed Size in *Vicia faba*: A Role for Seed Coat-Associated Invertases and Carbohydrate State", *The Plant Journal*, 1996, 10(5), pp. 823-834.

Weber, Hans et al., "Sugar Import and Metabolism During Seed Development", *Elsevier Science Ltd.*, 1997, vol. 2, No. 5, pp. 169-174.

Westgate. Mark E., "Carbohydrate Reserves and Reproductive Develoment at Low Leaf Water Potentials in Maize[1]", USDA-ARS and Department of Agronomy and Department of Plant Biology, Univ. of Illinois, Urbana, Ill., 1984, pp. 762-769.

Xu, Jian et al., "A Similar Dichotomy of Sugar Modulation and Developmental Expression Affects Both Paths of Sucrose Metabolism: Evidence from a Maize Invertase Gene Family", *The Plant Cell*, vol. 8, pp. 1209-1220.

Zhang, Long et al., "A Pea Cell-Wall Invertase Gene (Pslnv-1) With Tissue-Specific Expression", *Plant Physiology Biochemistry*, 1997, 35(10), pp. 751-760.

Zinselmeier, Chris et al., "Low Wsater Potential Disrupts Carbohydrate Metabolism in Maize (*Zea mays* L.) Ovaries[1]", *Plant Physiology*, 1995, vol. 35, No. 5, pp. 385-391.

Zinselmeier, Chris et al., "Reversing Drought-Induced Losses in Grain Yield: Sucrose Maintains Embryo Growth in Maize", *Crop Science*, 1995, 35:1390-1400.

Boyle, Mark G. et al., "Stem Infusion of Liquid Culture Medium Prevents Reproductive Failure of Maize at Low Water Potential", *Crop Science*, 1991, vol. 31, pp. 1246-1252.

Caddick, Mark X. et al., "An Ethanol Inducible Gene Switch for Plants Used to Manipulate Carbon Metabolism", *Nature Biotechnology*, 1998, vol. 16, pp. 177-180.

Doan, Danny N.P. et al., "Isolation of Molecular Markers from the Barley Endosperm Coenocyte and the Surrounding Nucellus Cell Layers", *Plant Molecular Biology*, vol. 31, pp. 877-886, Belgium.

Geiger, Donald R., et al., "Effect of Environmental Factors on Whole Plant Assimilate Partitioning and Associated Gene Expression", *Journal of Experimental Botany*, 1996, vol. 47, pp. 1229-1238.

Greene, Thomas W. et al., "Mutagenesis of the Potato ADP Glucose Pyrophosphorylase and Characterization of an Allosteric Mutant Defective in 3-Phosphoglycerate Activation", *Proc. Natl. Acad. Sci. USA*, 1996, vol. 93, pp. 1509-1513.

Griffith, S.M. et al., "Sugar Absorption and Metabolism By Immature Maize Endosperm and Embryo: A Working Model", *Department of Agronomy and Plant Genetics, University of Minnesota*, Paper No. 14,939, Scientific Journal Series, 1986, Poster 13, pp. 320-323.

Hampton, R.E. et al., "Fractionation and Purification of Cell Wall-Bound Invertase In Maize Ovaries", *USDA-ARS and U. of Minnesota*.

Hawker, J.S., "Sucrose, Biochemsitry of Storage Carbohydrates in Green Plants", 1985, *Academic Press*, pp. 1-51, London.

Herbers, Karin et al., "Manipulating Metabolic Partitioning in Transgenic Plants", *TIBTECH*, 1996, vol. 14.

Hoffman-Benning, S. et al., "Analysis of Growth, Composition and Thickness of the Cell Walls of Transgenic Tobacco Plants Expressing a Yeast-Derived Invertase", *Protoplasma*, 1997, 200: pp. 146-153.

Jenner, C.F., "Storage of Starch", pp. 700-745.

Koch, Karen E., et al., "Sugar and Metabolic Regulation of Genes for Sucrose Metabolism: Potential Influence of Maize Sucrose Synthase and Soluble Invertase Responses on Carbon Partitioning and Sugar Sensing[1]" *Journal of Experimental Botany*, 1996, vol. 47, pp. 1179-1185.

Kosegarten, Harald, et al., "Starch Deposition In Storage Organs and the Importance of Nutrients and External Factors", Institute of Plant Nutrition, Liebig-University Giessen, Germany, 1998, vol. 161, pp. 273-287.

\* cited by examiner

EXPRESSING ACID INVERTASE OR ADP-GLUCOSE PYROPHOSPHORYLASE IN FLORAL TISSUE FOR ENHANCED FLORAL SINK STRENGTH AND INCREASED STABILITY OF SEED IN PLANTS

CROSS-REFERENCE TO RELATED APPLICATION

This application claims the benefit of U.S. Provisional Application No. 60/140,314, filed Jun. 21, 1999 and U.S. application Ser. No. 09/599,353 filed on Jun. 20, 2000, now abandoned.

FIELD OF THE INVENTION

This invention relates generally to the field of plant molecular biology. More specifically, this invention relates to methods and reagents for the temporal and spatial expression of genes that enhance sink strength in plants, especially transgenic plants, to increase yield and health of plants in general as well as in periods of stress.

BACKGROUND OF THE INVENTION

The yield of a crop or ornamental plant ultimately depends on the energy the plant gains through the fixing of carbon dioxide ($CO_2$) into carbohydrates during photosynthesis. The primary sources of photosynthesis are the leaves, and to a lesser extent stem tissue. Other organs of the plant, such as roots, seeds or tubers, do not make a material contribution to the formation of photoassimilates, and instead are dependent for their growth on the supply of carbohydrates received from photosynthetically active organs. This means there is a flow in photosynthetically gained energy from photosynthetically active tissues to photosynthetically inactive tissues.

The direction of phloem transport of this energy is determined by the relative locations of the areas of supply and utilization of the products of photosynthesis. Translocation occurs from areas of supply (sources) to areas of metabolism or storage (sinks). Sources include any exporting organ, typically a mature leaf that is capable of producing photosynthate in excess of its own needs. Another type of source is a storage organ during the exporting phase of its development. For example a storage root may be a sink during the first growing season when it accumulates sugars received from the source leaves. During the second growing season the same root could become a source, when the stored sugars are remobilized and utilized to produce a new shoot which ultimately becomes reproductive. Sinks include any non-photosynthetic organs of the plant and organs that do not produce enough photosynthetic products to support their own growth or storage needs. Roots, tubers, developing fruits and immature leaves which must import carbohydrate for normal development are all examples of sink tissues. Sink tissues differ in their ability to attract source products. Elements such as stress, developmental stages of plant tissues, and osmotic potential all affect the transport of photoassimilates.

Differential distribution of photoassimilates within the plant is termed partitioning. Partitioning of assimilated carbon amongst sink organs is a critical factor that controls rate and pattern of plant growth. The regulation of the diversion of fixed carbon into the various metabolic pathways is termed allocation. The rate of fixed carbon in a source cell can be classified into three principle categories; storage, utilization, and transport. Starch is synthesized and stored within chloroplasts and in most species is a primary storage form that is mobilized for translocation during the night. Fixed carbon can be utilized within various compartments of the photosynthesizing cell to meet energy needs of the cell or provide carbon skeletons for the synthesis of other compounds required by the cells. Fixed carbon can also be incorporated into transport sugars for export to various sink tissues.

The rate of photosynthesis of leaves is strongly influenced by the demands of the sink. There are cases in which senescent leaves can be rejuvenated to full photosynthetic performance when the sink/source ratio is increased substantially. On the other hand rapid growth of a sink can sometimes compete with leaves for remobilizable nitrogen leading to senescent of the leaf and a drop in its photosynthetic capacity. Young leaves normally act as a sink rather than as a source. After a certain time however they begin to export carbohydrates to the phloem although import carbohydrate may continue for a while through different vascular strands. Once sucrose begins to actively load into companion cells and then into the sieve elements, water will enter by osmosis and flow will begin out of the line of veins. The leaf will become a source instead of a sink.

Two primary photoassimilates are sugar and starch, and these products are important to yield and plant development. Sugar and starch biochemistry are interrelated in plants. (See, e.g., Sivak, M. N. and J. Preiss (1994). Starch synthesis in seeds. In: *Seed development and germination*. Kigel, J. and G. Galili, eds. (Marcel Dekker, New York), pp. 139–168; J. S. Hawker (1985). Sucrose. In: *Biochemistry of storage carbohydrates in green plants*. P. M. Dey and R. A. Dixon, Eds., (Academic Press, London), pp. 1–51, which are incorporated herein by reference).

During the early development of storage organs, such as seeds and tubers, sucrose is imported and used for building the cellular components required for growth and development. Following this phase the metabolic program changes to convert the imported sucrose into storage compounds such as starch in tubers and fatty acids in oil seeds. Metabolism is finally altered to convert the starch and oils into reduced carbon compounds for the development of sprouts and seedlings respectively. Sucrose levels rise when hexoses decrease apparently terminating cell division in initiating differentiation and storage activities.

Early ear development relies upon concurrent photosynthate, as the developing seed cannot utilize stored photoassimilates present in other plant tissues. Because the seed are weak sinks, it is unable to attract stored reserves from source tissues. Seed abortion may occur when concurrent photosynthate is insufficient to meet the needs of reproductive growth, resulting in dramatically decreased yield, or in the case of maize ear, barrenness. The ability to manipulate source sink interactions to enhance sink strength of the ear and immature seed would make these reserves accessible, maintain seed growth, and as a consequence, buffer these important and vulnerable periods of yield formation during ear and early kernel development.

Anthesis is generally recognized as the critical period of ear and kernel development in maize. Varied experimental approaches demonstrate that treatments, which decrease the plant carbon exchange rate (CER) around anthesis, decrease grain yield. For example, large yield losses occur when maize plants are shaded (Early et al., 1967; Schussler and Westgate, 1991; Andrade et al., 1993), defoliated (Tollenaar and Daynard, 1978), subjected to water-deficits (Denmead and Shaw, 1960; Claassen and Shaw, 1970; Moss and Downey, 1971; Westgate and Boyer, 1986; Schussler and Westgate, 1991) or exposed to high plant density (Prine, 1971; Baenziger and Glover, 1980) around anthesis. Conversely, treatments that increase plant CER around anthesis increase grain yield. For example, yield enhancements are obtained when maize plants are provided supplemental radiation (Schoper et al., 1982; Ottman and Welch, 1988). In all cases, the variation in yield was directly related to the number of kernels that developed and supply of concurrent photosynthate. Collectively, these results suggest that kernel number may be limited by carbohydrate supply, particularly during drought stress at anthesis. According to the invention, enhancing sink strength of the immature ear and grain would make these limited assimilate supplies more accessible, maintain ear and seed growth, and as a consequence buffer this important vulnerable period of yield formation.

Traditional methods of improving yield formation have centered around breeding techniques. As with any valuable plant species, breeders have long used conventional breeding techniques to improve yield. While improvements have been achieved, breeding techniques are laborious and slow because of the time required to breed and grow successive plant generations. Furthermore, certain phenotypes may be impossible to obtain by conventional techniques. Thus, it would be desirable to utilize recombinant DNA technology to produce new plant varieties and cultivars in a controlled and predictable manner. It would be especially desirable to produce crop and ornamental plants with improved seed set over a range of environmental conditions to increase yield potential.

The partitioning of sucrose and starch is regulated by enzymes. Invertases are regarded as a control element in the changing carbohydrate status of seeds. Two enzymes are involved in catalyzing the cleavage process of sucrose, sucrose synthase and invertase. It has been proposed that each operates in a pathway of specific significance. In general, in sink tissues the invertase pathway is directed towards growth and cell expansion, whereas the sucrose synthase pathway is associated with storage product biosynthesis. Sucrose cleavage catalyzed by cell wall bound invertase occurs in the placento-chalazal cells of developing maize kernels. It has been implicated as a necessary step in either carbohydrate transport out of the vascular system or into the endosperm. Invertase activity seems to be important to early seed growth. The invertase pathway therefore appears to be associated with cell division and growth rather than storage.

Seed tissues actively engaged in storage often have a markedly low level of acid invertase activity but high levels of sucrose synthase activity. Sucrose synthase has frequently been cited as a marker for sink strength and the onset of starch synthesis is accompanied by an increase in enzyme activity.

In developing corn kernels a similar relationship between soluble acid invertase and import was evident during the very earliest phases of development. Both were associated with rapid rises in levels of mRNAs for soluble invertases which would be expected to peak prior to maximum accumulation in activity of the encoded enzyme. Sucrose synthase often predominates in starch/sucrose storage sinks while acid invertase predominates where cell expansion is active.

Starch synthesis takes place in the plastids of plant cells and involves ADP-Glucose Pyrophosphorylase (AGPase) which converts GIP into ADP-Glucose the direct precursor starch. AGPase is thought to control the starch-biosynthetic pathway in a number of plant species. Starch consists of two components. Linear helical amylose and branched amylopectin, both of which are glucose polymers. Amylose is composed of alpha-1, 4-glucans synthesized by granule bound starch synthase isoform 1 (GBSS1) which transfers the glucosyl residue from ADP-Glucose to alpha-1, 4-glucans. The combined action of soluble starch synthases and branching enzymes result in the production of amylopectin that contains additional alpha-1, 6-glycocytic branch plates.

Transgenic methods for affecting starch and sugar metabolism have been tried in plants. For example, transgenic tobacco plants over-expressing a yeast-derived invertase, one of several plant enzymes involved in sucrose metabolism, showed stunted internodal elongation, reduced leaf growth, and a disturbed sink-source relationship (See, e.g., Sonnewald, U., et al. (1991) *Plant J.* 1:95–106). Some of these deleterious effects could be obviated by using a chemically inducible plant gene expression system (Caddick, M. X., et al. (1998) *Nature Biotechnology*, 16:177–180).

In tomato, suppression or over-expression of acid invertase modified the sucrose content of fruit (Fitzmaurice, C. L., et al. (1991) International patent application number PCT/US92/01385; Bennett, A. B. and Klann, E. M. (1994) U.S. Pat. No. 5,658,773).

Constitutive expression of a yeast invertase in all cells of transgenic tobacco and potato plants modified the distribution of assimilates to effect changes in habit and yield (Willmitzer, L., et al., (1993) U.S. Pat. No. 5,658,773).

Antisense inhibition of AGPase reduced starch levels in transgenic potato tubers compared to wild-type (Müller-Röber, B., et al. (1992) EMBO J. 11:1229–1238).

Over-expression of an *E. coli* AGPase regulatory mutant in transgenic tobacco calli, tomato leaves, and potato tubers results in increased starch production (Kishore, G. M. (1991) International Patent application number PCT/US91/04036; Stark, D. M., et al. (1992) Science, 258:287–292).

Antisense inhibition of AGPase reduced starch and increased sucrose levels in pea (Gurgess, D. G. and Dooner, H. K. (1993) U.S. Pat. No. 5,498,831). Although these studies indicate importance of sucrose and starch metabolism, there remains a need in the art for a reliable transgenic method of increasing yield stability in plants.

It can be seen from the foregoing that a need exists in the art for a transgenic method of increasing yield potential in crop and ornamental plants.

It is an object of the present invention to provide expression constructs which when expressed in a temporal and spatial manner in a transgenic plant increase yield potential, as well as resistance to stress through regulation of sink strength.

It is yet another object of this invention to provide transgenic plant lines with heritable phenotypes which are useful in breeding programs designed to increase yield potential in crop plants over a range of environmental conditions.

It is yet another object of this invention to produce seed which will produce plants with increased yield potential.

It is yet another object of this invention to provide plants, plant cells, and plant tissues containing the expression constructs of the invention.

Other objects of the invention will become apparent from the description of the invention which follows.

SUMMARY OF THE INVENTION

The present invention comprises the spatial and temporal expression of a nucleotide sequence which will increase sink strength at critical times in plant development such as the vulnerable time of anthesis. In particular, this invention relates to polynucleotides which encode proteins involved in the starch and sucrose metabolic pathways, which are manipulated to maximize sink potential.

In one embodiment the invention comprises a genetic construct which upon expression in plant cells provides a DNA sequence encoding a gene product useful for increasing the sucrose flux or flow of a plant or plant tissue. In another embodiment the invention comprises a genetic construct which provides a DNA sequence encoding a gene product useful for affecting the starch content of a plant or plant tissue. The metabolic pathways of starch and sucrose synthesis and metabolism are well known and discussed at length in Stitt, Mark, "The Use of Transgenic Plants to Study the Regulation of Plant Metabolism", *Aust. J. Plant Physiol.*, 22:635–646 (1995); Herbers et al., "Manipulating Metabolic Partitioning in Transgenic Plants", *TIB TECH, June* 1996 (Vol. 14) pg. 198–205, the disclosures of which are hereby incorporated by reference.

For example invertase is an enzyme that plays a major role in controlling the flow of photoassimilates, such as sucrose, into sink tissues. According to the invention, transgenic expression of invertase can be accomplished at an appropriate time to increase the flow of photoassimilates into selected tissues at critical times such as anthesis and early grain development, thereby increasing the sink strength of these tissues. For another example, AGP is a key enzyme in the starch biosynthetic pathway. According to the invention transgenic expression of AGP is used to increase starch synthesis, thereby maintaining starch reserves. Expression of these enzymes is timed and spatially directed through the use of regulatory elements to increase sink strength at critical periods.

Kernel abortion increases when unfavorable environments occur around flowering, thereby decreasing genetic yield potential in plants. Developing female florets are weak sinks (relative to male florets) and compete less effectively when assimilate is limiting. The insoluble form of acid invertase is a critical enzyme that determines maize floral sink intensity by mediating assimilate unloading. Modification of female sink strength by altering the expression of insoluble acid invertase in a tissue and temporal specific manner should increase the likelihood of vigorous female floral development and also improve the consistency of seed set under unfavorable conditions.

Developing florets contain starch in the pedicel and ovary wall and these starch reserves are consumed when assimilate supply is restricted. Moreover, artificially feeding sucrose induces starch biosynthesis, indicating that these reserves are sensitive to assimilate supply and can be utilized for reproductive growth. Florets contain both starch biosynthetic and degradative capabilities. When unfavorable environments occur around flowering, starch degradation outpaces synthesis and these processes continue until starch is essentially consumed and reproduction fails (starch content at pollination and seed set are highly correlated). AGPase is a key regulatory enzyme in the starch biosynthetic pathway.

Thus the invention contemplates expression of sink strength enhancing nucleotide sequences during vulnerable periods primarily those involved with anthesis development, where yield is most significantly affected by stress.

As used herein the term "anthesis development" shall include any period in plant development where yield may be more significantly impacted by stress. This can include the exponential growth phase of the ear during which biomass is accumulated and the lag phase of kernel development as more fully described herein and in the following references. Set and Flower Synchrony within the Ear of Maize II. Plant Population Effects", *Crop Science,* 37: 448–455 (March-April 1997); and Shaw, Robert "Climate Requirement", *Corn Improvement,* 3$^{rd}$ ed., Chapter 10, pp. 609–638). As shown in FIG. 1, reprinted from *Corn and Corn Improvement*, plant yields are most vulnerable to moisture stress at a time period centered around flowering (0–10 DAP). Typically this period will be approximately 14 days prior to flowering through approximately 14 days after flowering.

The examples and discussion herein may specifically reference maize, however the teachings herein are equally applicable to any other grain or flowering crop.

As used herein the term "ear" shall not be limited to maize and shall include any developing female inflorescence from a planted.

As used herein the term "kernel" shall also not be limited to maize but shall include grain, or seed within a fruit.

As used herein the term "sink strength enhancing nucleotide sequence" shall mean any nucleotide sequence, (DNA, RNA, coding and/or antisense) the expression of which enhances a particular plant tissue's sink strength or ability to attract, maintain, or develop photosynthate resources, such as starch or sucrose.

According to the invention a genetic construct is disclosed which causes expression of the sink strength enhancing nucleotide sequence at a time and location to maximize sink strength typically during very vulnerable periods primarily such as anthesis development. The spatial and temporal expression of genes affecting, for example, the starch and sucrose content of tissues can be achieved using different types of promoters. Promoters useful for the invention are promoters which would cause the temporal and spatial expression of a gene product during anthesis development as defined herein and can be constitutive, inducible, or tissue specific.

For example seed specific promoters can be used to increase carbohydrate accumulation during seed development, pre-pollination promoters can also be used or stress inducible promoters can be used to increase carbohydrate reserves during periods of stress. The optimization of promoters to achieve the objectives of the invention is considered routine and easily ascertainable by those of skill in the art and is intended to be within the scope of the invention.

DESCRIPTION OF FIGURES

As shown in FIG. 1, reprinted from *Corn and Corn Improvement* from p. 614) of the relationship between age of crop and percentage yield decrement due to 1 day of moisture stress. The top and bottom lines represent the highest and lowest yield reductions obtained in stress experiments, the middle line the average reduction.

DETAILED DESCRIPTION OF THE INVENTION

Figure 1:
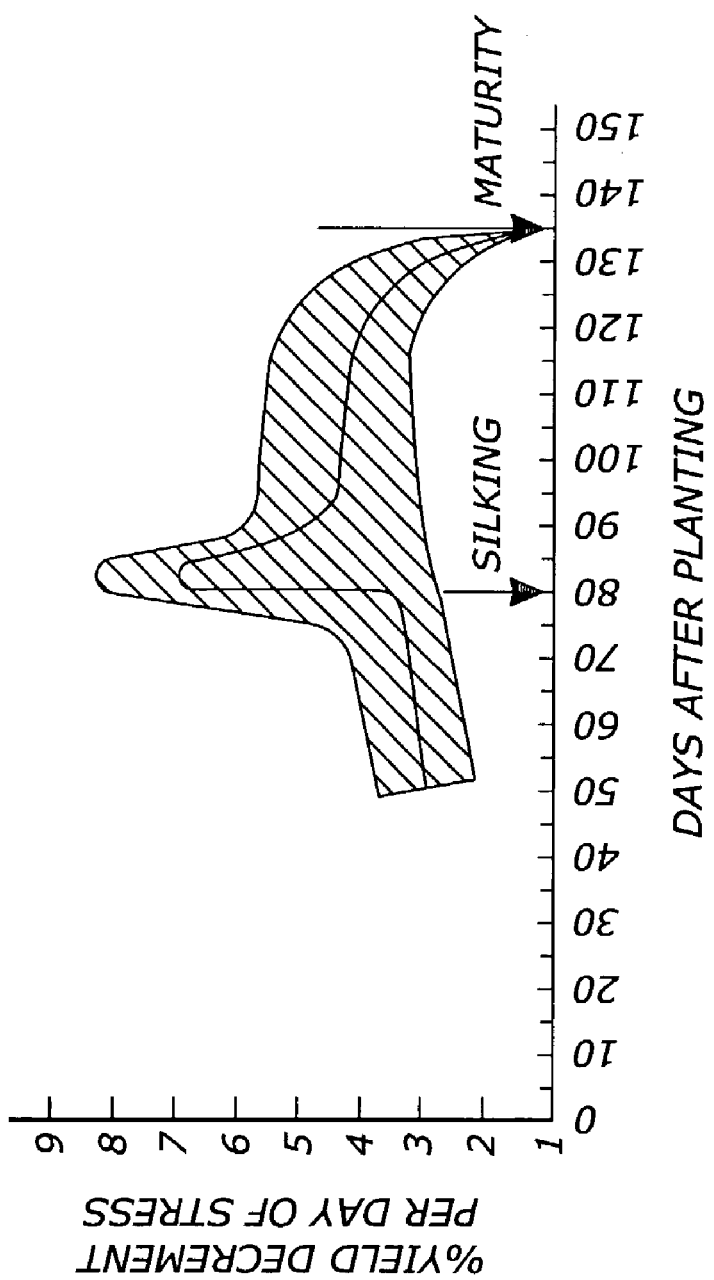
FIG. 1 is a schematic diagram (reproduced from Shaw, Robert "Climate Requirement", *Corn Improvement,* 3$^{rd}$ ed., Chapter 10, pp. 609–638).

The present invention is based on isolation and characterization of genes affecting the flux and availability of the photosynthate products which are sink strength enhancers such as starch and sucrose in plants. Any nucleotide sequence encoding an enzyme or metabolite in the starch or sucrose metabolic or anabolic pathways may be used in accordance with the present invention. Nucleotide sequences encoding these enzymes or substrates are easily ascertainable to those of skill in the art through Genbank or the references disclosed herein. For example, in starch storage organs of some plants, it is believed that sucrose is broken down in the cytoplasm into fructose plus UDP-glucose by sucrose synthase. UDP-glucose is then converted into glucose-1-phosphate by UDP-glucose pyrophosphorylase. Once in the amyloplasts of storage organs, glucose-1-phosphate is converted to ADP-glucose by (AGPase). ADP-glucose is then utilized by starch synthase to add a glucopyranosyl residue to the non reducing end of a glucan primer. An isoform of starch granule-bound enzyme has been implicated in the synthesis of amylose, the unbranched form of starch. Amylopectin, the branched form of starch, is formed by the combined actions of starch synthase and starch branching enzyme. Other reactions and pathways may be utilized by different organs in a plant (e.g., photosynthetic organs), or by different plant species. By changing the levels or activity of a component in a starch synthesis pathway (e.g., an enzyme or substrate) it is possible to affect the levels of sugar or starch in the plant, plant organ, or plant tissue.

At least three different types of invertases have been identified in plants: soluble and insoluble forms of invertase, and neutral invertase (See, e.g., ap Rees, T., "Sucrose Metabolism", Semin. Ser. Soc. Exp. Biol. Cambridge: Cambridge University Press 1984, Vol. 19, pp. 53–73 (1984). Soluble forms of acid invertase have been cloned and characterized from maize (See, e.g., Xu, J. et al. (1996) *Plant Cell* 8:1209–1220). Insoluble invertase has also been cloned from maize. Miller v. Chaterey, 1991, see also Shanker S. et al., *Plant Physiology* 108(2):873–874 (June 1995)in. A full length cDNA encoding a cell-wall-bound invertase was recently cloned from pea (See, e.g., Zhang, L., et al. (1997) *Plant Physiol. Biochem.*, 35:751–760, which is incorporated herein by reference). Several other invertases have been cloned and are easily accessible to those of skill in the art. See, Koch et al., "Sugar and Metabolic Regulation of Genes for Sucrose Metabolism", *J. of Experimental Botany*, Vol. 47, Special Issue, p. 1179–1185 (1996); these include Ivr 1 Genbank U16123, Ivr2 Genbank 031451, tomato soluble invertase Genbank Z12027, vicia faba soluble, Genbank Z49831, potato insoluble Z22645, carrot insoluble 1×81792, carrot insoluble 2×78424, maize insoluble 017695, Zymonionas 010465. See also Bennett, A. B., "Tomato acid invertase gene", WO 93/06711:7 October 1991 (1993); Elliott K., "Isolation and characterization of fruit vacuolar invertase genes from two tomato species and temporal differences in mRNA levels during fruit ripening", *Plant Molecular Biology* 21:515–524 (1993); Fitzmaurice, L., "Novel invertase gene(s) and uses thereof", WO 92/14831: 22 February 1991, Oct. 4, 1991 (1992); Fleischmacher, O. L., "Cell wall invertases from apex and callus tissues of sugar cane", *Plant and Cell Physiology* 21(7): 1273–1281 (1980); Hubbard, N. L., "Sucrose phosphate synthase and acid invertase as determinants of sucrose concentration in developing muskmelon (*Cucumis melo* L.) fruits", *Plant Physiol.* 91:1527–1534 (1989); Klann, E. M., "Acid invertase controls soluble sugar composition and fruit size in transgenic tomato", *Department of Vegetable Crops* 1–39; Klann, E. N., "Expression of acid invertase gene controls sugar composition in tomato (lycopersicon) fruit", *Plant Physiol.*, 103:863–870 (1993); Miron, D., "Sucrose Phosphate Synthase, Sucrose Synthase, and Invertase Activities in Developing Fruit of Lycopersicon esculentum Mill and the Sucrose Accumulating Lycopersicon hirsutum Humb. and Bonpl.", *Plant Physiol.* 95:623–627 (1991); Moriguchi, T., "Role of Sucrose Synthase and Other Related Enzymes in Sucrose Accumulation in Peach Fruit", *J. Jap. Soc. Hort. Sci.* 60(3):531–538 (1991); Ross, H. A., "Sucrose Metabolism in Tubers of Potato (solanum tuberosum L.)", *Plant Physiol.* 98:287–293 (1992); Stitt, M. A., "Sink" regulation of photosynthetic metabolism in transgenic tobacco plants expressing yeast invertase in their cell wall involves a decrease of the Calvin-cycle enzymes and an increase of glycolytic enzymes", *Planta* 183:40–50 (1990); Sung, S. S., "Growth, sucrose synthase, and invertase activities of developing Phaseolus vulgaris L. fruits", *Plant, Cell and Environment* 17:419-426 (1994).

AGP has been studied in plants and has been purified to varying degrees from spinach, maize, potato, rice, wheat, pea and barley (See, Sivak, M. N. and J. Preiss (1994). Starch synthesis in seeds. In: *Seed development and germination*. Kigel, J. and G. Galili, eds. (Marcel Dekker, New York), pp. 139–168). Complete or partial cDNAs for AGP have been cloned from wheat, corn, potato, rice, spinach, and barley (See, e.g., Bhave, M. R., et al. (1990) *Plant Cell* 2:531–538; Bae, J. M., et al. (1990) *Maydica* 3:317–322; and Nakata, P.A., et al. (1991) *Plant Mol. Biol.* 17:1089–1093, which are incorporated herein by reference). Complete cDNAs for AGP also have been cloned from yeast (Sonnewald, U., et al. (1991) *Plant J* 1:95–106, which is incorporated herein by reference) and bacteria. Preiss, J., "Bacterial Glycogen synthesis and its Regulation", *Ann. Rev. Microbiol.*, 38:419-58 (1984).

AGP is allosterically activated by 3-phosphoglycerate and inhibited by orthophosphate (See, e.g., Green, T. W., et al. (1996) *Proc. Natl. Acad. Sci.*, 93:1509-1513). Overexpression of an allosteric insensitive AGP would eliminate orthophosphate regulation of starch synthesis and may be useful in the invention for maintaining starch supplies when photosynthesis is inhibited. Giroux,-M. J.; Shaw, J.; Barry, G.; Cobb, B. G.; Green, T.; Okita, T.; Hannah, L.C., "A single gene mutation that increases maize seed weight", *Proc. Natl, Acad. Sci. U.S.A.*, Washington D.C.: National Academy of Sciences, Jun. 11, 1996, vol. 93 (12) p. 5824–5829; Green, T. W.; Kavakli, I. H.; Kahn, M. L. 1 Okita, T. W., "Generation of up-regulated allosteric variants of potato ADP-glucose pyrophosphorylase by reversion genetics", *Proc. Natl. Acad. Sci. U.S.A.*, Washington, D.C.: National Academy of Sciences, August, 1998, vol. 95, p. 10322–10327.

At its simplest the invention comprises a nucleotide construct comprising a sink strength enhancing nucleotide sequence, a regulatory promoter to regulate temporal tissue and spatial expression during anthesis development and termination sequences operably linked to said sink strength enhancing sequence.

A non exclusive list of enzymes that might be candidates for such intervention include sucrose synthase, starch-branching and starch-debranching enzymes, inorganic pyrophosphatase, sucrose phosphate synthase, soluble and insoluble forms of acid invertase, and ADPglucose pyrophosphorylase (AGP).

Identification of other polynucleotides which may be useful in the invention will typically be based on screening for procaryotic or eucaryotic organisms with altered levels of starch or sugar. For example, and not limitation, the mutant rb locus confers on pea embryos a reduction in starch and an increase in sugars (Kooistra, E. (1962) *Euphytica* 11:357–373), and is also associated with ten-fold reduced levels of AGP activity (Smith, A. M., et al. (1989) *Plant Physiol.* 89:1279–1284). Studies of isolated mutants of maize endosperm (i.e. Shrunken 2 and brittle 2) deficient in AGP activity are also deficient in starch content (See, Sivak, M. N. and J. Preiss (1994). Starch synthesis in seeds. In: *Seed development and germination*. Kigel, J. and G. Galili, eds. (Marcel Dekker, New York), pp. 139–168).

The polynucleotides useful in the invention can be formed from a variety of different polynucleotides (e.g., genomic or cDNA, RNA, synthetic oligonucleotides, and polynucleotides), as well as by a variety of different techniques. As used herein, a polynucleotide is a sequence of either eukaryotic or prokaryotic synthetic invention.

In a preferred embodiment the invention comprises use of one or more nucleotide sequences which, when expressed together enhance reproductive sink strength. This can allow for hybrid plant or seed production, once transgenic inbred parental lines have been established. For this embodiment the invention comprises a DNA sequence encoding an invertase enzyme capable of maintaining the sucrose concentration gradient critical in ensuring subsequent assimilate unloading into reproductive tissue or assimilate loading in critical, stress sensitive periods of plant development. In a second embodiment DNA sequence encoding AGP capable of maintaining starch synthesis, is provided for increasing yield, seed development, flowering or resistance to stress. The products of starch hydrolysis (glucose, glucose-6-phosphate, maltose etc. can act as osmotic agents influences the transport of photoassimilates.

The invention is not limited to any plant type and can be used for any crop or ornamental plant species for which it is desirable to increase yield. The methods of the invention may be applicable to any species of seed-bearing plant to enhance yield potential by affecting the sugar and starch content of sink tissue.

The nucleotide constructs of the present invention will share similar elements, which are well known in the art of plant molecular biology. For example, in each construct the DNA sequences of interest will preferably be operably linked (i.e., positioned to ensure the functioning of) to a promoter which allows the DNA to be transcribed (into an RNA transcript) and will comprise a vector which includes a replication system. In preferred embodiments, the DNA sequence of interest will be of exogenous origin in an effort to prevent co-suppression of the endogenous genes.

Promoters (and other regulatory elements) may be heterologous (i.e., not naturally operably linked to a DNA sequence from the same organism). Promoters useful for expression in plants are known in the art and can be inducible, constitutive, tissue-specific, derived from eukaryotes, prokaryotes or viruses, or have various combinations of these characteristics.

In choosing a promoter to use in the methods of the invention, it may be desirable to use a tissue-specific or developmentally regulated promoter. A tissue-specific or developmentally regulated promoter is a DNA sequence which regulates the expression of a DNA sequence selectively in the cells/tissues of a plant critical to seed set and/or function and/or limits the expression of such a DNA sequence to the period of seed maturation in the plant. Any identifiable promoter may be used in the methods of the present invention which causes expression during anthesis development as defined herein. It may also be advantageous to use a stress inducible promoter to provide expression of the construct during periods of stress.

Differential screening techniques can be used to isolate promoters expressed in developing female reproductive organs prior to, and immediately after, flowering (0–10 DAP). Promoters identified in this manner include NUC1 which is expressed in the nucleus prior to fertilization (Doan, D. N. P., et al. (1996) *Plant Mol. Biol.* 31:877–886, which is incorporated herein by reference).

Promoters which are preferred for the invention and would be acceptably timed to anthesis development follow. These and other such promoters are known and accessible through sources such as Genbank: barley promoter B22E: 69 NAL Call No. 442.8 Z34 "Primary Structure of a Novel Barley Gene Differentially Expressed in Immature Alleurone Layers," Klemsdae, S. S. et al., Springer Int'l 1991 Aug., *Molecular and General Genetics*, Vol. 228(1/2) p. 9–16, 1991. Expression of B22E is specific to the pedicel in developing maize kernels, Zag2: 134 NAL Call. No.: QK725.P532 Identification and molecular characterization of ZAG1, the maize homolog of the Arabidopsis floral homeotic gene AGAMOUS. Schmidt, R. J.; Veit, B.; Mandel, M. A.; Mena, M.; Hake, S.; Yanofsky, M. F. Rockville, Md.: American Society of Plant Physiologists, c1989-; 1993 Jul. The Plant Cell v. 5(7): p 729–737; 1993 Jul. includes references. Zag2 transcripts can be detected 5 days prior to pollination to 7 to 8 DAP, and directs expression in the carpel of developing female inflorescences and Cim1 which is specific to the nucleus of developing maize kernels. Cim1 transcript is detected 4 to 5 days before pollination to 6 to 8 DAP. Other useful promoters include any promoter which can be derived from a gene whose expression is maternally associated with developing female florets.

Table 1 shows a list of preferred promoters including their timing of expression (DAP=days after pollination).

Promoter Expression Summary

| Promoter | Source | Primary Tissue | Temporal |
|---|---|---|---|
| ltp2 | barley cDNA | aleurone | <6–24+ DAP |
| cim1 | maize EST | pericarp (under silk scar) | 0–12+ DAP |
| nuc1-c | barley cDNA | nucleus, pedicel forming region | 1–12+ DAP |
| mze40-2 [maize B22e] | maize EST | gloom, pericarp, pedicel forming region, low in scutellum | <4–28+ DAP |
| b22e | barley genomic | aleurone, embryo scutellum, pedicel forming region | <5–30+ DAP |
| zag2 | maize, EST | floret, ovule | <0–22 DAP |
| end1 | maize, cDNA | endosperm transfer cells | 6–14 DAP |
| bet11 | maize, cDNA | endosperm transfer cells | 8–30+ DAP |

Figure 2:
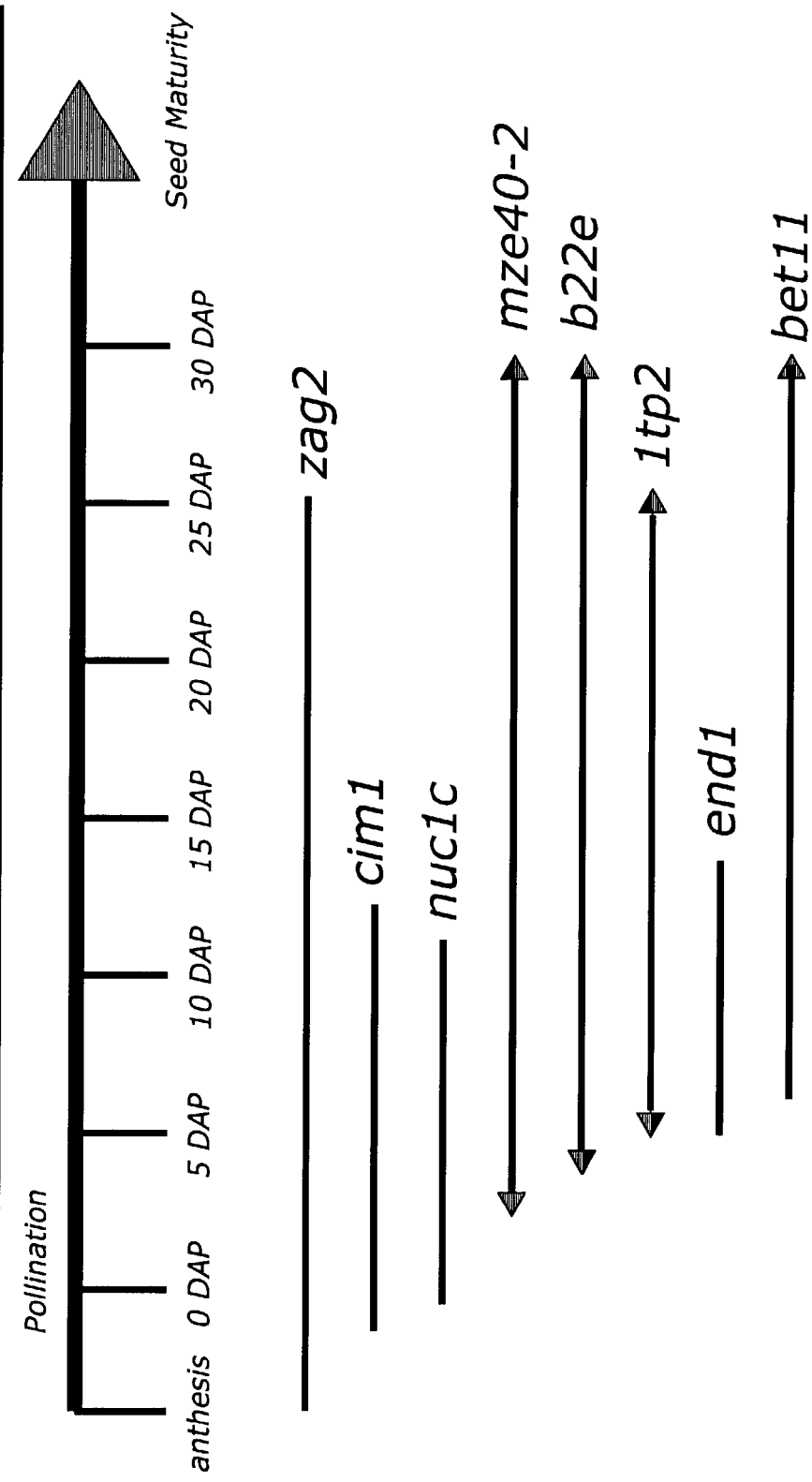
FIG. 2 is a chart depicting expression timing of various promoters useful for the present invention.

FIG. 2 also depicts the timing of various preferred promoters and kernel development.

For example a construct useful for the present invention might include the maize soluble invertase gene operably linked to the B22e promoter for expression of invertase 5 to 28 days after pollination.

Other promoters which are seed or embryo specific and may be useful in the invention include patatin (potato tubers) (Rocha-Sosa, M., et al. (1989) *EMBO J.* 8:23–29), convicilin, vicilin, and legumin (pea cotyledons) (Rerie, W. G., et al. (1991) *Mol. Gen. Genet.* 259:149–157; Newbigin, E. J., et al. (1990) Planta 180:461–470; Higgins, T. J. V., et al. (1988) *Plant. Mol. Biol.* 11:683–695), zein (maize endosperm) (Schemthaner, J.P., et al. (1988) *EMBO J.* 7:1249–1255), phaseolin (bean cotyledon) (Segupta-Gopalan, C., et al. (1985) *Proc. Natl. Acad. Sci. U.S.A.* 82:3320–3324), phytohemagglutinin (bean cotyledon)

(Voelker, T. et al. (1987) *EMBO J.* 6:3571–3577), B-conglycinin and glycinin (soybean cotyledon) (Chen, Z-L, et al. (1988) *EMBO J.* 7:297–302), glutelin (rice endosperm), hordein (barley endosperm) (Marris, C., et al. (1988) *Plant Mol. Biol.* 10:359–366), glutenin and gliadin (wheat endosperm) (Colot, V., et al. (1987) *EMBO J.* 6:3559–3564), and sporamin (sweet potato tuberous root) (Hattori, T., et al. (1990) *Plant Mol. Biol.* 14:595–604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in Arabidopsis and *Brassica napus* seeds (Vanderkerckhove et al., *Bio/Technology* 7:L929–932 (1989)), been lectin and bean β-phaseolin promoters to express luciferase (Riggs et al., *Plant Sci.* 63:47–57 (1989)), and wheat glutenin promoters to express chloramphenicol acetyl transferase (Colot et al., *EMBO J.* 6:3559–3564 (1987)).

Any inducible promoter can be used in the instant invention. See Ward et al. *Plant Mol. Biol.*22: 361–366 (1993). Exemplary inducible promoters include, but are not limited to, that from the ACEI system which responds to copper (Mett et al. *PNAS* 90: 4567–4571 (1993)); In2 gene from maize which responds to benzenesulfonamide herbicide safeners (Hershey et al., *Mol. Gen. Genetics* 227: 229–237 (1991) and Gatz et al., *Mol. Gen. Genetics* 243: 32–38 (1994)) or Tet repressor from Tn10 (Gatz et al., Mol. Gen. Genet. 227: 229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88: 0421 (1991).

Many different constitutive promoters can be utilized in the instant invention. Exemplary constitutive promoters include, but are not limited to, the promoters from plant viruses such as the 35S promoter from CaMV (Odell et al., *Nature* 313: 810–812 (1985) and the promoters from such genes as rice actin (McElroy et al., *Plant Cell* 2: 163–171 (1990)); ubiquitin (Christensen et al., *Plant Mol. Biol* 12: 619–632 (1989) and Christensen et al., *Plant Mol. Biol.* 18: 675–689 (1992)): pEMU (Last et al., *Theor. Appl. Genet.* 81: 581–588 (1991)); MAS (Velten et al., *EMBO J.* 3: 2723–2730 (1984)) and maize H3 histone (Lepetit et al., *Mol. Gen. Genet.* 231: 276–285 (1992) and Atanassova et al., *Plant Journal* 2 (3): 291–300 (1992)).

The ALS promoter, a XbaI/NcoI fragment 51 to the Brassica napus ALS3 structural gene (or a nucleotide sequence that has substantial sequence similarity to said XbaI/NcoI fragment), represents a particularly useful constitutive promoter. See PCT application WO96/30530.

Transport of protein produced by transgenes to a subcellular compartment such as the chloroplast, vacuole, peroxisome, glyoxysome, cell wall or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art. See, for example, Sullivan, T., "Analysis of Maize Brittle-1 Alleles and a Defective Suppressor-Mutator-Induced Mutable Allele", *The Plant Cell*, 3:1337–1348 (1991), Becker et al., *Plant Mol. Biol.* 20: 49 (1992), Close, P.S., Master's Thesis, Iowa State University (1993), Knox, C., et al., "Structure and Organization of Two Divergent Alpha-Amylase Genes From Barley", *Plant Mol. Biol.* 9: 3-17 (1987), Lerner et al., *Plant Physiol.*91: 124–129 (1989), Fontes et al., *Plant Cell* 3: 483-496 (1991), Matsuoka et al., *Proc. Natl. Acad. Sci.* 88: 834 (1991), Gould et al., *J. Cell Biol* 108: 1657 (1989), Creissen et al., *Plant J.* 2: 129 (1991), Kalderon, D., Robers, B., Richardson, W., and Smith A., "A short amino acid sequence able to specify nuclear location", *Cell* 39: 499–509 (1984), Stiefel, V., Ruiz-Avila, L., Raz R., Valles M., Gomez J., Pages M., Martinez-Izquierdo J., Ludevid M., Landale J., Nelson T., and Puigdomenech P., "Expression of a maize cell wall hydroxyproline-rich glycoprotein gene in early leaf and root vascular differentiation", *Plant Cell* 2: 785–793 (1990).

Selection of an appropriate vector is relatively simple, as the constraints are minimal. The minimal traits of the vector are that the desired nucleic acid sequence be introduced in a relatively intact state. Thus, any vector which will produce a plant carrying the introduced DNA sequence should be sufficient. Typically, an expression vector contains (1) prokaryotic DNA elements encoding for a bacterial replication origin and an antibiotic resistance marker to provide for the growth and selection of the expression vector in a bacterial host; (2) DNA elements that control initiation of transcription, such as a promoter; (3) DNA elements that control the processing of transcripts such as transcription termination/polyadenylation sequences; and (4) a reporter gene. Useful reporter genes include β-glucuronidase, β-galactosidase, chloramphynical acetyltransferase, luciferase, kanamycin or the herbicide resistance genes PAT and BAR. Preferably the reporter gene is kanamyacin or the herbicide resistance genes PAT and BAR. The BAR or PAT gene is used with the selecting agent Bialaphos, and is used as a preferred selection marker gene for plant transformation (Spencer, et al. (1990) *J. Thero. Appl'd Genetics* 79:625–631).

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80: 4803 (1983). Another commonly used selectable marker gene is the hygromycin phosphotransferase gene which confers resistance to the antibiotic hygromycin. Vanden Elzen et al., *Plant Mol. Biol.*, 5: 299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86: 1216 (1988), Jones et al., *Mol. Gen. Genet.*, 210: 86 (1987), Svab et al., *Plant Mol. Biol.* 14: 197 (1990), Hille et al., *Plant Mol. Biol.* 7: 171 (1986). Other selectable marker genes confer resistance to herbicides such as glyphosate, glufosinate or broxynil. Comai et al., *Nature* 317: 741–744 (1985), Gordon-Kamm et al., *Plant Cell* 2: 603–618 (1990) and Stalker et al., Science 242: 419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13: 67 (1987), Shah et al., *Science* 233: 478 (1986), Charest et al., *Plant Cell Rep.* 8: 643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5: 387 (1987)., Teeri et al., *EMBO J.* 8: 343 (1989), Koncz et al., *Proc. Natl. Acad. Sci. U.S.A.* 84:131 (1987), De Block et al., *EMBO J.* 3: 1681 (1984). Another approach to the identification of relatively rare transformation events has been use of a gene that encodes a dominant constitutive regulator of the *Zea mays* anthocyanin pigmentation pathway. Ludwig et al., *Science* 247: 449 (1990).

Recently, in vivo methods for visualizing GUS activity that do not require destruction of plant tissue have been made available. Molecular Probes Publication 2908, Imagene Green, p. 1–4 (1993) and Naleway et al., *J. Cell Biol.* 115: 151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

Genes included in expression vectors must be driven by a nucleotide sequence comprising a regulatory element, for example, a promoter. Several types of promoters are now well known in the transformation arts, as are other regulatory elements that can be used alone or in combination with promoters.

A general description of plant expression vectors and reporter genes can be found in Gruber, et al. (Gruber et al. (1993) Vectors for Plant Transformation. In: *Methods in Plant Molecular Biology and Biotechnology*. Glich et al., eds. (CRC Press), pp. 89–119.

Expression vectors containing genomic or synthetic fragments can be introduced into protoplast or into intact tissues or isolated cells. Preferably expression vectors are introduced into intact tissue. General methods of culturing plant tissues are provided for example by Maki, et al. (Maki, et al. (1993) Procedures for Introducing Foreign DNA into Plants: In: *Methods in Plant Molecular Biology & Biotechnology*; Glich et al. eds. (CRC Press), pp. 67–88; Philips, et al. (1988) Cell-Tissue Culture and In Vitro Manipulation. In *Corn & Corn Improvement*, 3rd ed. Sprague, et al. eds. (American Society of Agronomy Inc.), pp. 345–387).

Methods of introducing expression vectors into plant tissue include the direct transfection or co-cultivation of plant cell with *Agrobacterium tumefaciens* (Horsch et al. (1985) *Science*, 227:1229). Descriptions of Agrobacterium vector systems and methods for Agrobacterium-mediated gene transfer are provided by Gruber et al. (supra).

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89–119.

A. Agrobacterium-Mediated Transformation

One method for introducing an expression vector into plants is based on the natural transformation system of Agrobacterium. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10: 1 (1991). Descriptions of Agrobacterium vector systems and methods for Agrobacterium-mediated gene transfer are provided by Gruber et al., supra, Miki et al., supra, and Moloney et al., *Plant Cell Reports* 8: 238 (1989). See also, U.S. Pat. No. 5,591,616, issued Jan. 7, 1997.

B. Direct Gene Transfer

Despite the fact the host range for Agrobacterium-mediated transformation is broad, some major cereal crop species and gymnosperms have generally been recalcitrant to this mode of gene transfer, even though some success has recently been achieved in rice and maize. Hiei et al., *The Plant Journal* 6: 271–282 (1994); U.S. Pat. No. 5,591,616, issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 mm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J.C., *Trends Biotech.* 6: 299 (1988), Klein et al., *Bio/Technology* 6: 559–563 (1988), Sanford, J. C., *Physiol Plant* 79: 206 (1990), Klein et al., *Biotechnology* 10: 268 (1992). In maize, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology* 9: 996 (1991). Alternatively, liposome or spheroplast fusion have been used to introduce expression vectors into plants. Deshayes et al., *EMBO J.*, 4: 2731 (1985), Christou et al., *Proc Natl. Acad. Sci. U.S.A.* 84: 3962 (1987). Direct uptake of DNA into protoplasts using CaCl2 precipitation, polyvinyl alcohol or poly-L-ornithine have also been reported. Hain et al., *Mol. Gen. Genet.* 199: 161 (1985) and Draper et al., *Plant Cell Physiol*.23: 451 (1982). Electroporation of protoplasts and whole cells and tissues have also been described. Donn et al., In Abstracts of VIIth International Congress on Plant Cell and Tissue Culture IAPTC, A2–38, p 53 (1990); D'Halluin et al., *Plant Cell* 4: 1495–1505 (1992) and Spencer et al., *Plant Mol. Biol.* 24: 51–61 (1994).

Following transformation of maize target tissues, expression of the above-described selectable marker genes allows for preferential selection of transformed cells, tissues and/or plants, using regeneration and selection methods now well known in the art.

After transformation of a plant cell or plant, plant cells or plants transformed with the desired DNA sequences integrated into the genome can be selected by appropriate phenotypic markers. Phenotypic markers are known in the art and may be used in this invention.

Confirmation of transgenic plants will typically be based on an assay or assays or by simply measuring growth rate. Transformed plants can be screened by biochemical, molecular biological, and other assays. Various assays may be used to determine whether a particular plant, plant part, or a transformed cell shows an increase in enzyme activity or carbohydrate content. Typically the change in expression or activity of a transformed plant will be compared to levels found in wild type (e.g., untransformed) plants of the same type. Preferably, the effect of the introduced construct on the level of expression or activity of the endogenous gene will be established from a comparison of sibling plants with and without the construct. AGP and acid invertase levels can be measured for example by Northern blotting, primer extension, quantitative or semi-quantitative PCR (polymerase chain reaction), and other methods well known in the art (See, e.g., Sambrook, et al. (1989). *Molecular Cloning, A Laboratory Manual*, second edition (Cold Spring Harbor Laboratory Press), Vols. 1–3). Protein can be measured in a number of ways including immunological methods (e.g., by Elisa or Western blotting). AGP activity can be measured in various assays as described in Smith (Smith, A.M. (1990). In: *Methods in Plant Biochemistry*, Vol. 3, (Academic Press, New York), pp. 93–102). Sugar content of a plant cell or tissue can be measured in a variety of ways including those described in Zinselmeier, et al. (Zinselmeier, C., et al. (1995) *Plant Physiol.* 107:385–391).

Normally, regeneration will be involved in obtaining a whole plant from a transformation process. The term "regeneration" as used herein, means growing a whole plant from a plant cell, a group of plant cells, a plant part, or a plant piece (e.g., from a protoplast, calys, or a tissue part).

The foregoing methods for transformation would typically be used for producing transgenic inbred lines. Transgenic inbred lines could then be crossed, with another (non-transformed or transformed) inbred line, in order to produce a transgenic hybrid maize plant. Alternatively, a genetic trait which has been engineered into a particular maize line using the foregoing transformation techniques could be moved into another line using traditional backcrossing techniques that are well known in the plant breeding arts. For example, a backcrossing approach could be used to move an engineered trait from a public, non-elite line into an elite line, or from a hybrid maize plant containing a foreign gene in its genome into a line or lines which do not contain that gene. As used herein, "crossing" can refer to a simple X by Y cross, or the process of backcrossing, depending on the context.

Various plants will be suitable targets for enhancing sink strength in female reproductive organs with the acid invertase and AGP genes. In particular, the methods of the invention described herein may be applicable to any crop species including but not limited to barley, sorghum, wheat, maize, soybean, and rice.

In a most preferred embodiment, transformation is carried out in maize plants according to the method of agrobacterium.

Parts obtained from the regenerated plant, such as flowers, pods, seeds, leaves, branches, fruit, and the like are covered by the invention, provided that these parts comprise cells which have been so transformed. Progeny and variants, and mutants of the regenerated plants are also included within the scope of this invention, provided that these parts comprise the introduced DNA sequences.

Sucrose levels, starch levels and the activity of acid invertase and AGP are preferably determined as set forth in the examples.

Once a transgenic plant is produced having a desired characteristic, it will be useful to propagate the plant and, in some cases, to cross to inbred lines to produce useful hybrids.

In seed propagated crops, mature transgenic plants may be self crossed to produce a homozygous inbred plant. The inbred plant produces seed containing the genes for the newly introduce trait. These seeds can be grown to produce plants that will produce the selected phenotype. All articles cited herein and in the following list are hereby expressly incorporated in their entirety by reference.

CITATIONS

U.S. Pat. No. 5,436,395 (Jul. 25, 1995) Willmitzer et al., "Plasmid for the Preparation of Transgenic Plants with a Change in Habit and Yield"

U.S. Pat. No. 5,498,831 (Mar. 12, 1996) Burgess et al., "Pea ADP-Glucose Pyrophosphorylase Subunit Genes and Their Uses"

U.S. Pat. No. 5,658,773 (Aug. 19, 1997) Bennett et al., "Tomato Acid Invertase Gene"

Boyle, Mark G., "Stem infusion of liquid culture medium prevents reproductive failure of maize at low water potential", *Crop Science,* 1991, 31:1246–1252

Caddick, Mark X., "An ethanol inducible gene switch for plants used to manipulate carbon metabolism", *Nature Biotechnology,* 1998, 16:177–180

Doan, Danny N. P., "Isolation of molecular markers from the barley endosperm coenocyte and the surrounding nucellus cell layers", *Plant Molecular Biology,* 1996, 31:877

Geiger, Donald R., "Effect of environmental factors on whole plant assimilate partitioning and associated gene expression", *Journal of Experimental Botany,* 47, Special Issue, pp. 1229–1238, August 1996

Green, Thomas W., "Mutagenesis of the potato ADPglucose pyrophosphorylase and characterization of an allosteric mutant defective in 3-phosphoglycerate activation", *Proc. Nat. Acad. Sci. USA,* 1996, 93:1509–1513

Griffith, S. M., "Sugar absorption and metabolism by immature maize endosperm and embryo: a working model", Poster 13, Regulation of Carbon and Nitrogen Reduction and Utilization in Maize, J. C. Shannon, D. P. Knievel and C. D. Boyer, Eds., 1986, The American Society of Plant Physiologists, 320–323

Hampton, R. E., R. J. Jones and M. E. Westgate, "Fractionation and purification of cell wall-bound invertase in maize ovaries", *Crop Science Divisions, p.* 127

Herbers, Karin, "Mainpulating metabolic partitioning in transgenic plants", TIBTECH, June 1996 14: 198–205

Hoffmann-Benning, S., "Analysis of growth, composition and thickness of the cell walls of transgenic tobacco plants expressing a yeast-derived invertase", *Protoplasma* 1997 200:146–153

Koch, Karen E., "Sugar and metabolic regulation of genes for sucrose metabolism: potential influence of maize sucrose synthase and soluble invertase responses on carbon partitioning and sugar sensing", *Journal of Experimental Botany*, 47, Special Issue, pp. 1179–1185, August 1996

Kosegarten, Harold, "Starch deposition in storage organs and the importance of nutrients and external factors", *Z. Pfanzenernahr. Bodenk.*, 161: 273–287 (1998)

Miller, Michael E., "The maize invertase-deficient miniature-1 seed mutation is associated with aberrant pedicel and endosperm development", *The Plant Cell*, 1992, 4:297

Schmalstig, Judy Gougler, "Transport and metabolism of a sucrose analog (1'-fluorosucrose) into *Zea mays* L. Endosperm without Invertase Hydrolysis", Plant Physiol. 1987, 85:902–905

Schussler, J. R., "Maize kernel set at low water potential: I. sensitivity to reduced assimilates at pollination", *Crop Science*, 1991, 31:1196–1203

Stitt, Mark, "The use of transgenic plants to study the regulation of plant carbohydrate metabolism", *Aust. J. Plant Physiol.*, 1995, 22: 635–46

Weber, Hans, "Controlling seed development and seed size in Viciafaba: a role for seed coat-associated invertases and carbohydrate state", *The Plant Journal*, 1996, 10(5), 823–834

Weber, Hans, "Sugar import and metabolism during seed development", *Trends in Plant Science*, May 1997, Vol. 2 (5)

Westgate, M. E., R. E. Hampton, and R. J. Jones, "Influence of water deficit on acid invertase activity and apoplastic environment in maize ovaries", *Crop Science Divisions*, Division C-3, p. 136.

Westgate, Mark E., "Carbohydrate reserves and reproductive development at low leaf water potentials in maize", *Crop Science*, 1985, 25:762–769

WO 96/14421 (05/17/96) Barry, et al., "Tomato Fruit Promoters"

Xu, Jian, "A similar dichotomy of sugar modulation and developmental expression affects both paths of sucrose metabolism: evidence from a maize invertase gene family", *The Plant Cell*, 1996, 8:1209–1220

Zhang, Long, "A pea cell-wall invertase gene (Pslnv-1) with tissue-specific expression", *Plant Physiol. Biochem.*, 1997, 35:10, 751–760

Zinselmeier, C., "Reversing drought-induced losses in grain yield: sucrose maintains embryo growth in maize", *Crop Science*, 1995, 35:5 1390–1400

Zinselmeier, Chris, "Low water potential disrupts carbohydrate metabolism in maize (*Zea mays* L.) ovaries", *Plant Physiol.* 1995, 107:385–391

What is claimed is:

1. An expression construct comprising:
a polynucleotide encoding acid invertase or ADP-glucose pyrophosphorylase operably linked to a promoter selected from the group consisting of zag2, b22e, and end1;
wherein a transgenic plant comprising said construct displays enhanced seed yield under abiotic stress conditions compared to the seed yield of a plant isogenic except for said construct and grown under the same stress conditions.

2. A method of enhancing seed yield in a plant under abiotic stress, said method comprising:
transforming a plant cell with a genetic construct, said construct comprising a polynucleotide which encodes a protein selected from the group consisting of acid invertase and ADP-glucose pyrophosphorylase, operably linked to a promoter selected from the group consisting of: zag2, b22e, and end1;
culturing said plant cell under plant cell growing conditions; and
regenerating from said cultured plant cell a transformed plant,
wherein said transformed plant displays enhanced seed yield under abiotic stress conditions, compared to the seed yield of a plant isogenic except for said construct and grown under the same stress conditions.

* * * * *